United States Patent [19]

Snedden

[11] Patent Number: 4,810,194
[45] Date of Patent: Mar. 7, 1989

[54] DISPOSABLE ANTISEPTIC DENTAL SHIELD

[76] Inventor: John E. Snedden, Box 398 - 107 N. 1st Ave., Sandpoint, Id. 83864

[21] Appl. No.: 116,647

[22] Filed: Nov. 4, 1987

[51] Int. Cl.$^4$ .......................... A61C 1/16; A61C 17/04
[52] U.S. Cl. ....................................... 433/91; 433/116; 433/28
[58] Field of Search ............... 604/349, 171, 172, 902; 128/132 R; 433/116, 46, 91, 93, 94, 95

[56] References Cited

U.S. PATENT DOCUMENTS

| | | | |
|---|---|---|---|
| 268,996 | 6/1882 | Brinkerhoff | 188/113 |
| 738,960 | 6/1903 | Vaughan et al. | 206/306 |
| 1,120,549 | 3/1914 | Schellberg | 604/171 |
| 2,623,523 | 11/1952 | Benson | 604/199 |
| 3,335,723 | 8/1967 | Waldman, Jr. | 604/163 |
| 3,673,868 | 6/1972 | Beury, III et al. | 374/158 |
| 4,241,828 | 1/1980 | Bourdelle et al. | 206/306 |
| 4,266,935 | 5/1981 | Hoppe | 433/116 |
| 4,327,735 | 5/1982 | Hampson | 604/171 |
| 4,569,344 | 1/1986 | Palmer | 128/207.16 |
| 4,696,296 | 9/1987 | Palmer | 604/171 |

Primary Examiner—Robert Peshock
Attorney, Agent, or Firm—Wells, St. John & Roberts

[57] ABSTRACT

Antiseptic dental shields for preventing contamination of hand-held dental devices with infective micro-organisms or other pathogenic substances are disclosed. Such shields comprise an elongated disposable sanitary sleeve which cover at least a substantial portion of exterior surfaces of the hand-held dental devices. The sleeves are flexible, transparent, and sufficiently thin for accommodating manual manipulation of controls on the hand-held dental devices while maintaining sterility thereof. A disposable hanger adapter can be employed to connect with existing hangers which conveniently mount hand-held dental devices to further prevent contaminants from being transferred from one dental patient to another.

16 Claims, 6 Drawing Sheets

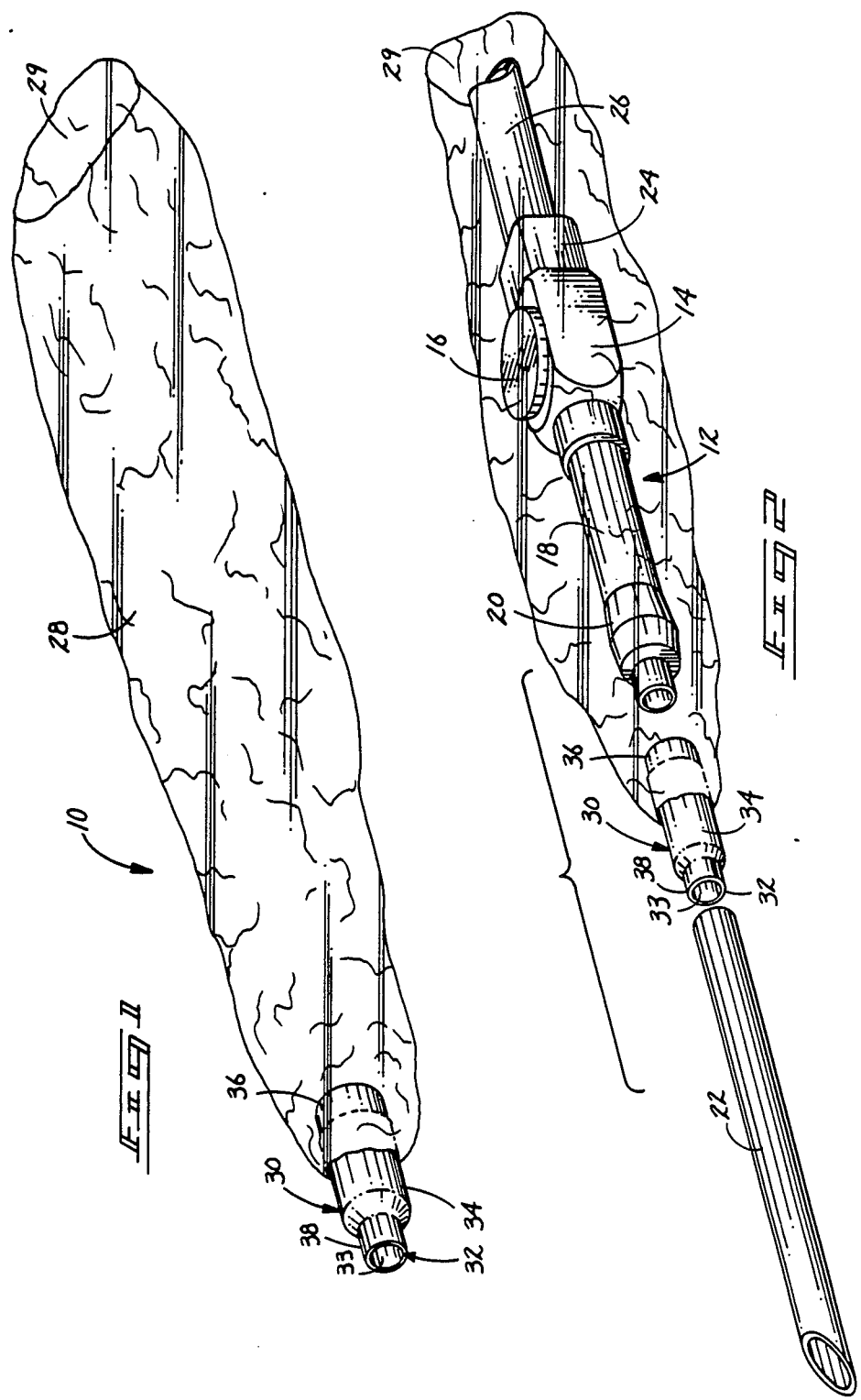

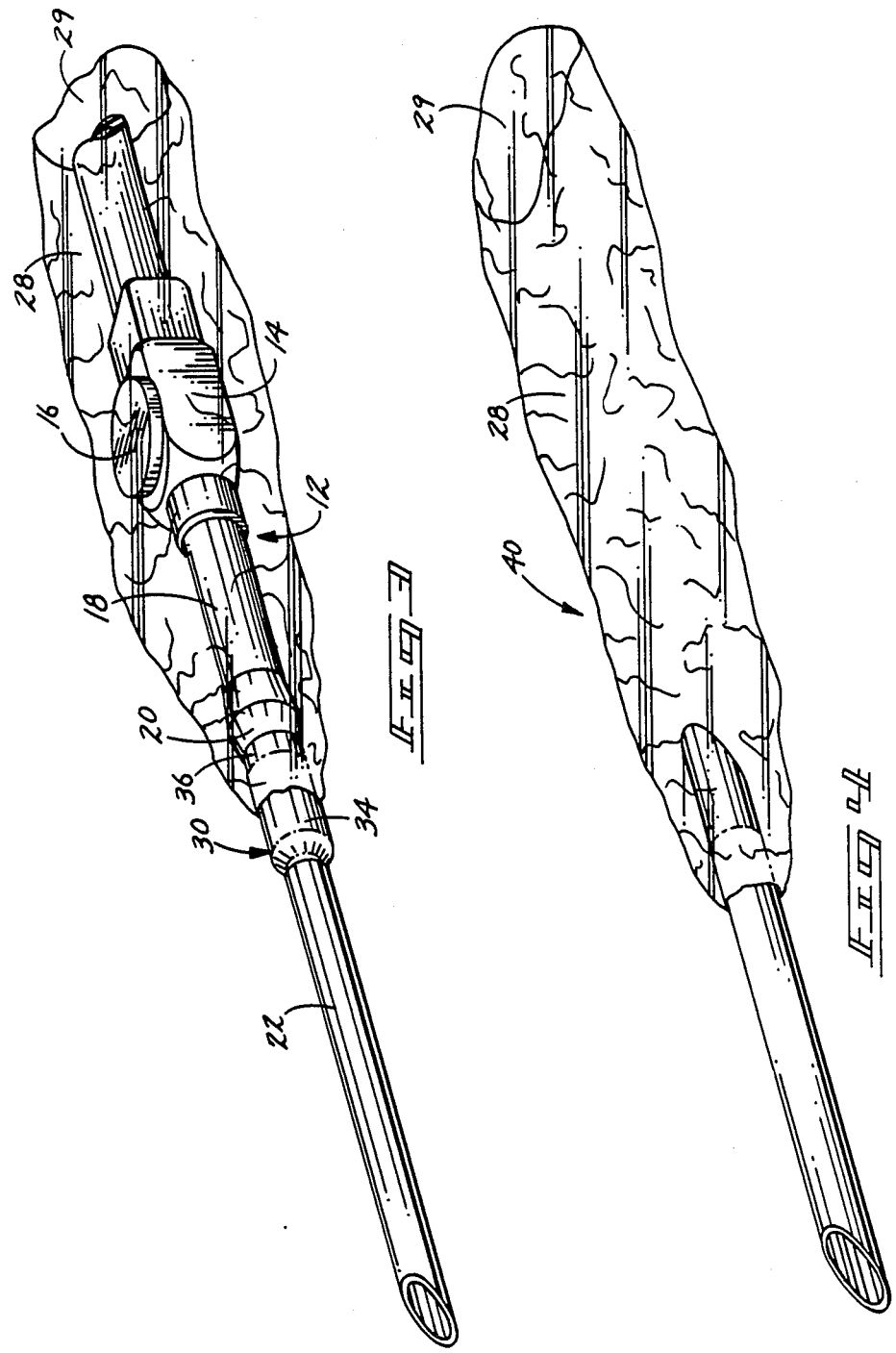

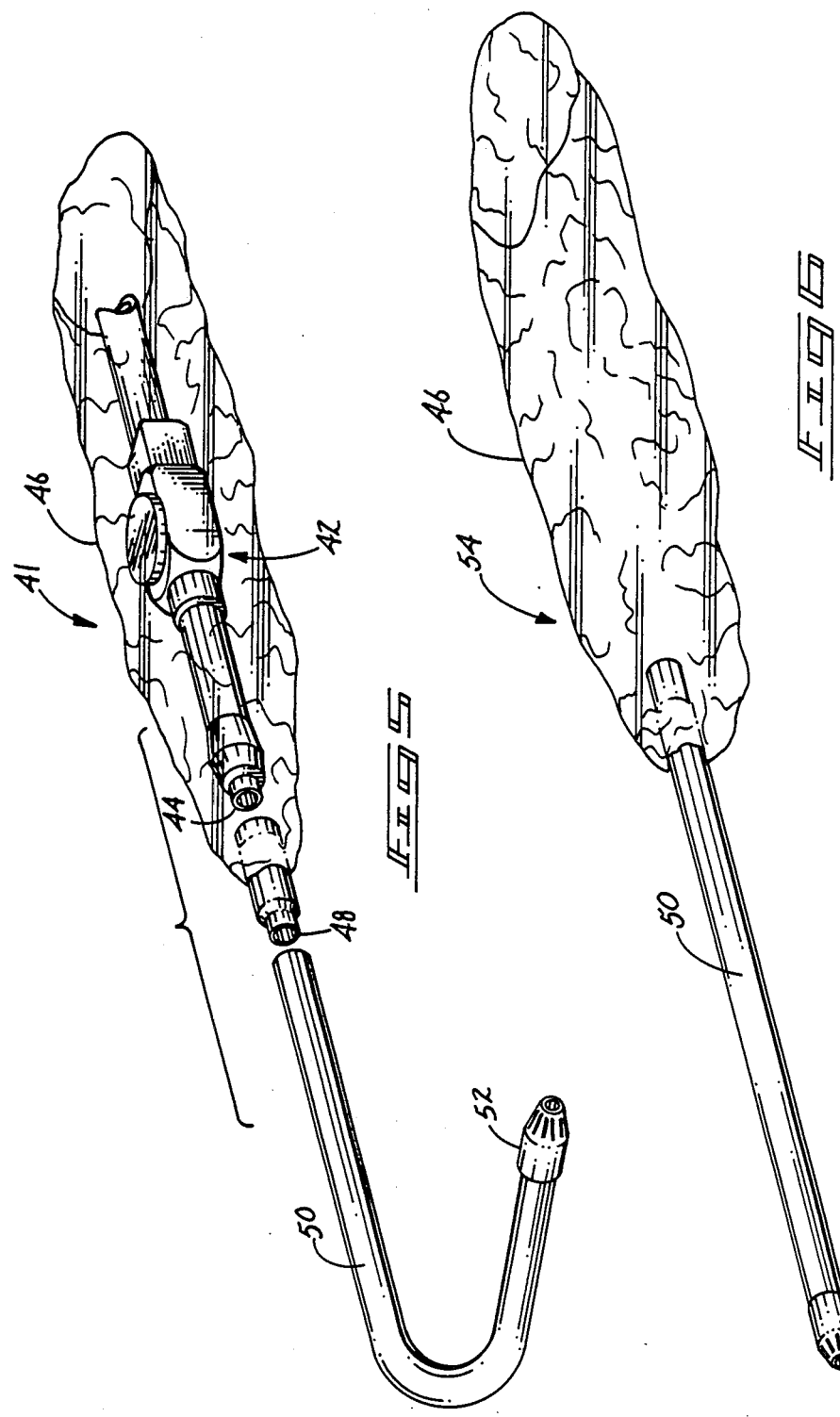

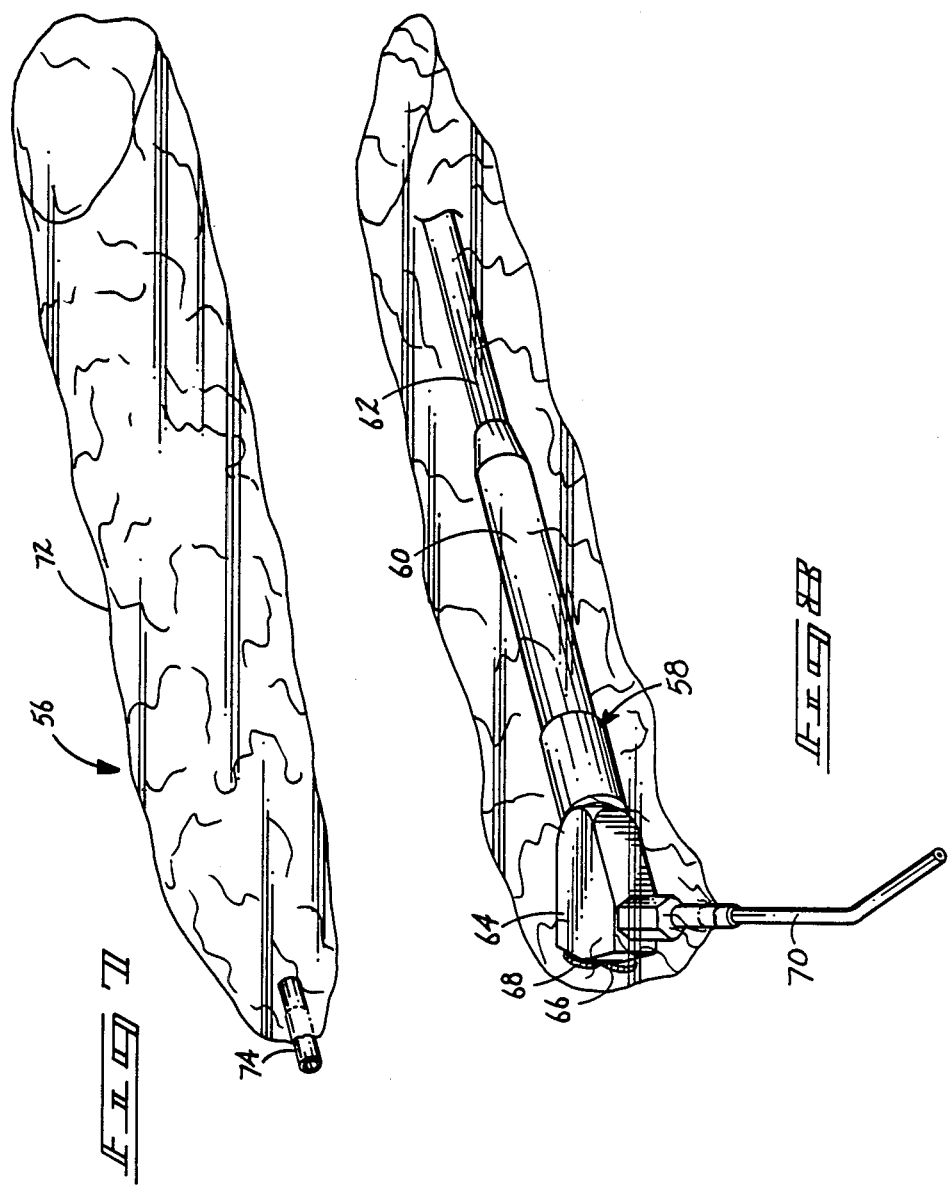

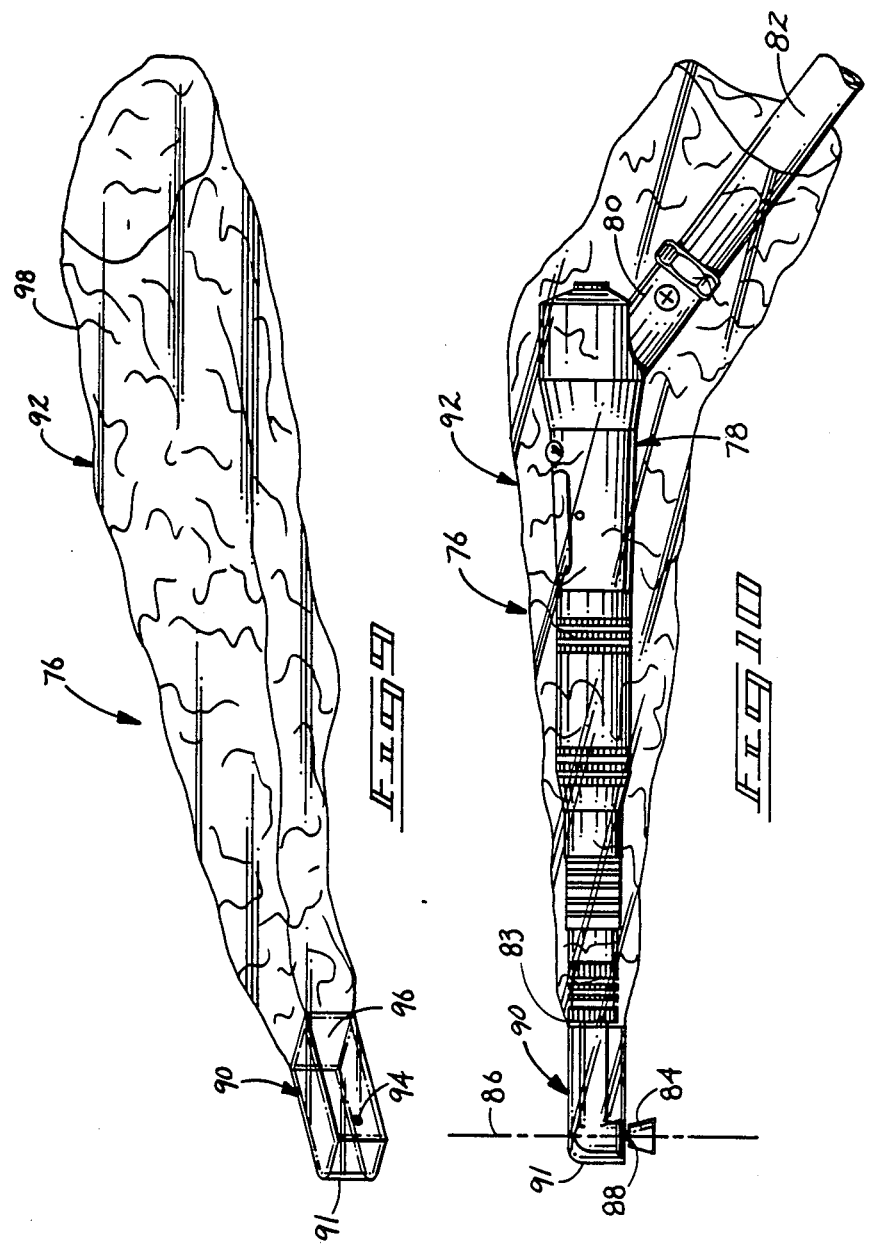

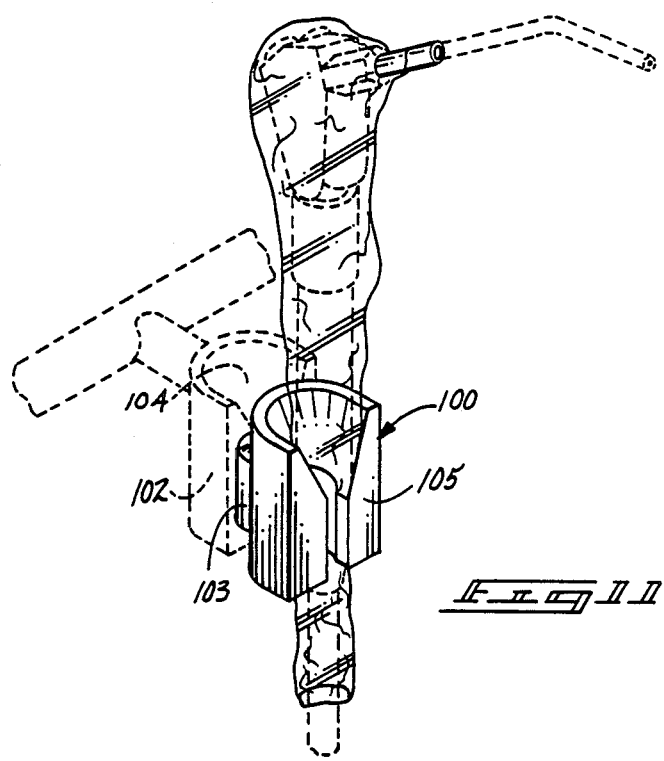
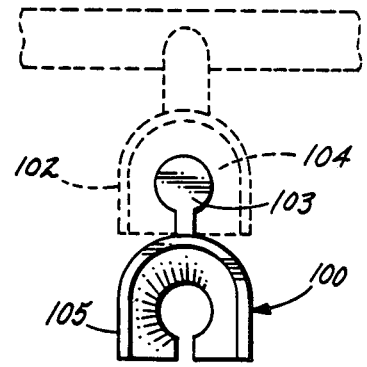

DISPOSABLE ANTISEPTIC DENTAL SHIELD

TECHNICAL FIELD

This invention relates to sterility of hand-held dental devices.

BACKGROUND OF THE INVENTION

Dentists typically use a variety of powered hand-held dental devices. Such dental devices are typically longitudinally elongated and are adapted for receiving a removable end piece at one end thereof for performing a specific dental function. The end opposite the removable end piece connects to a utility supply hose.

One such dental device comprises a rotary dental hand piece commonly used for drilling, shaping and cleaning teeth. Such devices are typically air driven, and supplied with air through the utility hose.

Another hand-held dental device is the combination air-water injection syringe. This device typically includes a removable metal end tube through which air or water is injected into the patient's mouth. The tube is made to be removable for cleaning between uses on different patients.

Yet another type of powered hand-held dental device is the suction tool which is used for removing saliva and other liquids from the patient's mouth while the dentist or hygienist performs a dental function. These liquid evacuation devices typically employ disposable, hollowed end tubes which extend into the patient's mouth. The tube is made disposable for ease of use and sanitation purposes.

While performing a dental function with such devices, it is not uncommon for human fluid to be emitted outwardly from the patient's mouth. Additionally, the dentist's hands typically come into contact with fluid within the patient's mouth. Such fluid can contain germs or other pathogenic substances such as the AIDS virus and hepatitis. These substances can contaminate the hand-held dental devices either directly from the patient's mouth or from the dentist's or hygienist's hands.

The removable end pieces on all such hand-held dental devices are normally changed between uses on different patients. However, the hand-held portions of the devices and utility hose connected thereto are typically not changed or sterilized between uses. Consequently, there can be a transmission of bacteria, viruses, etc., from one patient to another via the hands of the dentist by the touching of a contaminated hand-held device or hose connected thereto.

Accordingly, a need remains for preventing contamination of hand-held dental devices with infective microorganisms or other pathogenic substances to prevent transfer of such substances from one dental patient to another.

BRIEF DESCRIPTION OF THE DRAWINGS

Preferred embodiments of the invention are illustrated in the accompanying drawings, in which:

FIG. 1 is a perspective view of a dental shield and adapter for use with a high volume dental evacuator device in accordance with the invention;

FIG. 2 is an exploded view of the dental shield and adapter of FIG. 1 illustrated positionally relative to a disposable end tube and valve mechanism of a high volume dental evacuator device;

FIG. 3 is an assembled view of the components of FIG. 2;

FIG. 4 is a perspective view of a disposable end piece for a high volume dental evacuation system employing a dental shield in accordance with the invention;

FIG. 5 is an exploded perspective view of an alternate embodiment adapter and dental shield employed with a low volume evacuation device and associated disposable end tube;

FIG. 6 is a perspective view of a disposable low volume evacuation tube employing a dental shield in accordance with the invention;

FIG. 7 is a perspective view of a dental shield and adapter specifically configured for use with a conventional combination air-water injection syringe;

FIG. 8 is a perspective view of a conventional combination air-water injection syringe employing the dental shield and adapter of FIG. 7;

FIG. 9 is a perspective view of a dental shield specifically adapted for use with a powered rotary dental hand piece;

FIG. 10 is a side elevational view of a rotary dental hand piece employing the dental shield of FIG. 9;

FIG. 11 is a perspective view of an antiseptic hanger adapter employed with a conventional hand-held dental device hanger in accordance with the invention; and FIG. 12 is a top view of FIG. 11.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

The invention comprises a disposable antiseptic dental shield having an elongated disposable sanitary sleeve which covers at least a substantial portion of the exterior surfaces of a hand-held dental device. The sleeve is substantially impervious to transmission of viruses, bacteria, or other microorganisms and pathogenic substances to prevent transfer of such substances to the hand-held dental devices and subsequently to dental patients.

Referring to FIGS. 1-3, an antiseptic dental shield 10 in accordance with the invention is illustrated for shielding a high-volume evacuator or suction device 12. Evacuator device 12 includes a valve body 14 having a valve control 16 for regulating the amount of suction. An elongated hollow tube 18 extends longitudinally outward from one end of valve body 14. An annular ring 20 surrounds an exterior portion of tube 18 adjacent its outermost end. The outermost end is sized for connection with a disposable high-volume evacuator tube 22 which is placed in the patient's mouth. The remaining end of valve body 14 includes a shorter longitudinally extending portion 24 which receives a suction hose 26 for evacuating fluid therethrough from the dental patient's mouth.

Antiseptic dental shield 10 includes an elongated disposable sanitary sleeve 28 and an adapter 30. Sleeve 28 is flexible and longitudinally collapsible. Its internal diameter is typically 2½ to 3½ inches to easily accommodate evacuator device 12 therein. Sleeve 28 is typically constructed of a substantially transparent and sufficiently thin material for accommodating manual manipulations of valve control 16 on valve body 14 while still maintaining sterility. An example of such a material is a thin plastic such as polyethylene which is less than one millimeter in thickness. A thickness of approximately ½ millimeter is preferred.

Sleeve 28 includes an axial opening 29 at one end. The end opposite the one end is connected to adapter 30 which engages the disposable high-volume evacuator tube 22. Adaptor 30 is comprised of a short tubular piece having external surfaces 34, and a hollowed central portion 32 defined by internal surfaces 33. Central portion 32 defines a passageway through which fluid flows to evacuator device 12.

Adaptor 30 includes a first end 36 which is sized to sealingly connect to the outermost portion of tube 18 extending from valve body 14. A second end 38, opposite first end 36, is narrower in diameter than end 36 and is sized the same as the outer end of tube 18 to sealingly receive disposable tube 22 thereabout. Accordingly, fluid flows from the dental patient's mouth through evacuator tube 22, adapter 30, evacuator device 12 and into suction tube 26 for disposal.

Sleeve 28 connects to exterior surfaces 34 of adapter 30 to seal the sleeve relative thereto. Sleeve 28 can be connected to adapter 30 by any suitable means such as taping, heat sealing, adhesive bonding, or otherwise. Sleeve 28 is longitudinally extendible from adapter 30 for covering at least a substantial portion of exterior surfaces of evacuator device 12. As illustrated, sleeve 28 has a length which is greater than the longitudinal length of evacuator device 12 to shield the exterior surfaces of evacuator device 12 along its entire length, as well as to shield a portion of suction hose 26 connected thereto. Antiseptic dental shield 10 is preferably constructed to be disposable along with evacuator tube 22.

Antiseptic dental shield 10 can be installed by inserting evacuator device 12 through opening 29 of sleeve 28 and connecting adapter 30 onto tube 18 and against annular ring 20. Sleeve 28 is then longitudinally extended its full length to cover evacuator 12 and a portion of hose 26. Evacuator tube 22 is then sealing inserted onto adapter 30.

FIG. 4 illustrates an alternate apparatus 40 wherein a sleeve 28 is directly connected to exterior surfaces of a disposable tubular adapter 22 providing one complete disposable unit for use by the dentist or hygienist.

FIG. 5 illustrates an alternate dental shield apparatus 41 specifically adapted for use with a low volume evacuator device 42. Low volume evacuator device 42 is similar to high volume evacuator device 12 but for a lower capacity. Accordingly, an outermost end 44 of evacuator device 42 includes a smaller diameter opening and internal fluid passageway than that passageway of large volume evacuator device 12.

Dental shield 41 also includes an open-ended sleeve 46 which sealingly connects to exterior surfaces of an adaptor 48. Sleeve 46 and adaptor 48 are substantially the same as the sleeve and adapter of dental shield 10 for a large volume evacuator device except for being correspondingly reduced in size. Low volume evacuator devices typically receive an associated smaller diameter disposable end piece 50. End piece 50 is typically a flexible member having a bendable wire (not shown) extending therethrough which enables the tube to be bent into a variety of shapes for hooking into the patient's mouth. A suction tip 52 is illustrated as being connected to the outermost end of end piece 50.

FIG. 6 illustrates an alternate shield 54 wherein sleeve 46 is directly connected to exterior surfaces of a disposable low volume evacuator tube 50 providing one complete disposable unit for use by the dentist or hygienist.

FIGS. 7 and 8 illustrate yet another embodiment antiseptic dental shield apparatus 56 specifically adapted to be used with a conventional combination air-water injection syringe 58. Syringe 58 is typically used by a dentist or hygienist to inject air or water into the patient's mouth to clean the surfaces where the densist is working, or for rinsing the patient's mouth. Syringe 58 includes a longitudinally elongated body 60 connected at one end to a utility hose 62 which supplies the necessary air and water. The end of body 60 opposite the hose connection end includes a valve assembly 64. Valve assembly 64 includes a pair of push-button valve controls 66, 68, one of which controls injection of water, the other of which controls injection of air. A metal tube 70, which is typically non-disposable and adapted to be inserted into the dental patient's mouth, extends outwardly from valve assembly 64 in convenient angled fashion. It typically includes two internal passageways (not shown), one of which communicates water, the other of which communicates air to the patient's mouth. Valve control buttons 66, 68 are operated independently or simultaneously for emitting air or water, or an air-water mixture, through tube 70 into the patient's mouth as desired.

Dental shield 56 is also comprised of a longitudinally elongated, flexible and collapsible open-ended sleeve 72 which is sealingly secured to exterior surfaces of an adapter 74. Adapter 74 is a longitudinally elongated, hollow tube having an internal diameter which is sized to be slidably received about removable end piece 70. Sleeve 72 extends longitudinally rearward from adapter tube 74 to shield the exterior surfaces of air-water injection syringe 58. Sleeve 72 also extends rearwardly a sufficient distance to shield a portion of utility hose 62 connected thereto.

FIGS. 9 and 10 illustrate yet another embodiment dental shield apparatus 76 specifically adapted for use with a conventional air-driven dental hand piece 78. Hand piece 78 is longitudinally elongated having a connection extension 80 angled from one end. Extension 80 is adapted to connect to an air supply hose 82. The opposite end of rotary dental hand piece 78 receives a removable right angle drive unit 83. The outermost end of right angle drive 83 receives and rotates a work piece 84 about a rotation axis 86 which is substantially perpendicular to the longitudinal orientation of hand piece 78. Work piece 84 typically includes an integral drive shaft 88 extending rearwardly therefrom which removably connects to right angle drive 83. Right angle drives are typically removable from the dental hand piece and adapted for receiving different work pieces and for operating at different speeds.

Dental shield 76 is illustrated as being comprised of first and second portions 90, 92, respectively. First portion 90 is comprised of a substantially rigid, preferably hard plastic, rectangularly elongated shell which surrounds the outermost end portion of right angle drive 83. An upper outermost end 91 of shell 90 is rounded to generally conform to the rounded shape of that particular portion of right angle drive 83 which the shell covers. A hole 94 extends through a bottom portion or wall adjacent the outer end of shell 90 for rotationally receiving drive shaft 88 of work piece 84. Hole 94 is preferably just slightly larger than the diameter of shaft 88 to minimize transfer of pathogenic substances to the right angle drive. The rearwardmost portion of shell 90 includes a rectangular opening 96.

Certain right angle drives employ a locking chuck for locking shaft 88 of certain work pieces relative to the right angle drive. Such chucks are typically accessed along rotation axis 86 from the top or rear of the right angle drive. To accommodate such right angle drives, a hole (not shown) can be provided through shell 90 along axis 86 at the wall opposite the wall through which hole 94 extends.

Second portion 92 comprises a flexible, longitudinally collapsible sleeve which is sealingly joined to shell 90 about rectangular opening 96 of shell 90. Sleeve portion 92 extends longitudinally rearwardly from shell 90 to shield the exterior surfaces of rotary dental hand piece 78. Sleeve portion 92 also preferably extends a sufficient distance beyond rotary dental hand piece 78 to cover a portion of air supply hose 82. Accordingly, the combined longitudinal lengths of the first and second portions is preferably sufficiently great to shield the rotary hand piece exterior surfaces along its entire length, as well as to shield a portion of the air hose connected thereto.

FIGS. 11 and 12 illustrate the structure of a hanger adapter component 100 for use in conjunction with an air-water injection syringe 58. Hand-held dental devices are typically removably mounted to an appropriately sized hanger 102 when not in use at a location easily accessible by the dentist or dental hygienist. Hangers 102 are typically tapered C-shaped in lateral cross-section including a central opening 104 having a slot at it's forward end. The hand-held dental device is lowered into and retained by this C-shaped section. If germs are present on the hand-held dental devices when placed in the hanger, such germs can easily be transferred to the hanger. Germs on the hanger could then be transferred to otherwise clean dental shields and subsequently transferred from patient to patient.

A disposable hanger adapter 100 is preferably employed with hangers 102 to prevent such hangers from passing germs to the hand-held dental devices. Hanger adapters 100 include a male projection 103 which is lockingly received within hanger opening 104. The remaining portion of adapter 100 includes a lateral C-shaped hanger projection 105 of the same size and configuration of hanger 102 for receiving a particular hand-held dental device. Male projection 103 defines a first engaging means for connecting the hanger adapter to the hanger. Hanger projection 105 defines a second engaging means for receiving a hand-held dental device from the hanger to prevent transfer of pathogenic substances. The hanger adapters are preferably constructed to be disposed after completing the dental work on each patient.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. An antiseptic dental shield for preventing contamination of a hand-held dental device with infective microorganisms or other pathogenic substances to prevent transfer of such substances from one dental patient to another, the hand-held dental device being longitudinally elongated and having a longitudinal length, and being adapted for receiving a removable end piece at one longitudinal end thereof, the opposite longitudinal end being adapted for connection to a utility supplying hose, the removable end piece being specifically adapted for insertion into a patient's mouth for performing a dental function, the shield comprising:

an elongated disposable sanitary sleeve for covering at least a substantial portion of exterior surfaces of the hand-held dental device, the sleeve being substantially impervious to transmission of pathogenic substances;

wherein the sleeve has a length which is greater than the longitudinal length of the hand-held dental device to shield exterior surfaces of the hand-held dental device along its entire length, and to shield a portion of a utility hose connected to the dental device; and an antiseptic hanger adapter for a hanger upon which a hand-held dental device is normally receivable, the hanger adapter including first engaging means for connecting the hanger adapter to the hanger, and second engaging means for receiving the covered hand-held dental device to separate the covered hand-held dental device from the hanger.

2. An antiseptic dental shield for preventing contamination of a dental evacuator device which evacuates fluid from a dental patient's mouth by suction, the evacuator device having one end which is normally adapted for receiving a disposable evacuator tube piece which extends into a dental patient's mouth, the end opposite the one end receiving a vacuum hose which is connected to a vacuum source, the shield comprising:

a disposable hollow tubular adapter having opposed longitudinal ends, one of the adapter ends being sized and shaped for sealing engagement with the one end of the evacuation device, the other of the adapter ends being sized and shaped for sealing engagement with the disposable evacuator tube piece which extends into the dental patient's mouth; and an elongated sanitary sleeve having one end sealed to the adapter and being longitudinally extendible from the adapter to cover and shield exterior surfaces of the evacuator device, the sleeve and adapter being substantially impervious to pathogenic substances.

3. The dental shield of claim 2 wherein the sleeve has a length which is greater than a longitudinal length of the evacuator device to shield exterior surfaces of the evacuator device along its entire length, and to shield a portion of a hose which is connected to the evacuator device.

4. The apparatus of claim 2 wherein the evacuator device has an enlarged one end for handling a large volume of fluid from the dental patient's mouth, the adapter being sized for connection with the enlarged one end of the evacuator device and the disposable evacuator tube piece.

5. The dental shield of claim 2 wherein the evacuator device has a small diameter one end for handling a small volume of fluid from the dental patient's mouth, the adapter being sized for connection with the small diameter one end of the evacuator device and the disposable evacuator tube piece.

6. The dental shield of claim 2 wherein a substantial portion of the sleeve is flexible, substantially transparent, and sufficiently thin for accommodating manual manipulation of a valve control on the evacuator device while maintaining sterility.

7. The dental shield of claim 2 wherein the sleeve has a length which is greater than a longitudinal length of the evacuator device to shield exterior surfaces of the evacuator device along its entire length, and to shield a portion of the hose which is connected to the evacuation device; and a substantial portion of the sleeve being flexible, substantially transparent, and sufficiently thin for accommodating manual manipulation of a valve control on the evacuator device while maintaining sterility.

8. The antiseptic dental shield as defined in claim 2 wherein the elongated sanitary sleeve is cylindrical having an internal diameter of between 2½ inches and 3⅛ inches inclusive.

9. The antiseptic dental shield as defined in claim 2 wherein the one end of the evacuator device and the other end of the adapter have substantially the same diameter with the one end of the evacuator device receiving the one end of the adapter and the one end of the adapter receiving the disposable evacuator tube piece.

10. The antiseptic dental shield as defined in claim 9 wherein the one end of the evacuator device is cylindrical having a prescribed diameter and wherein the one end of the adapter has a cylindrical internal surface that slidably fits over the one end of the evacuator device and wherein the other end of the adapter has an external cylindrical surface substantially equal to the prescribed diameter of the one end of the evacuator device for slidably inserting into the rear end of the disposable evacuator tube piece.

11. A disposable dental fluid evacuation apparatus specifically adapted for attachment to a dental evacuator device for evacuating dental fluid from a dental patient's mouth by suction, the apparatus comprising:

a disposable elongated evacuator tube piece having internal and external surfaces, the internal surfaces defining a passageway through which fluid flows from the dental patient's mouth to the dental evacuator device; and an elongated sanitary sleeve having an end sealed to the exterior surfaces of the evacuator tube piece and extending longitudinally from the evacuator tube piece for covering exterior surfaces of the dental evacuator device, the sleeve being substantially impervious to pathogenic substances.

12. The dental apparatus of claim 11 wherein the sleeve has a length which is greater than a longitudinal length of the dental evacuator device to shield exterior surfaces of the evacuator device along its entire length, and to shield a portion of a suction hose which is connected to the evacuator device.

13. The dental apparatus of claim 11 wherein a substantial portion of the sleeve is flexible, substantially transparent, and sufficiently thin for accommodating manual manipulation of a valve control on the evacuator device while maintaining sterility.

14. The dental apparatus of claim 11 wherein the sleeve has a length which is greater than a longitudinal length of the evacuator device to shield exterior surfaces of the evacuator device along its entire length, and to shield a portion of a suction hose which is connected to the evacuator device; and wherein a substantial portion of the sleeve is flexible, substantially transparent, and sufficiently thin for accommodating manual manipulation of a valve control on the evacuator device while maintaining sterility.

15. The dental apparatus of claim 11 wherein the evacuator device has an enlarged one end for handling a large volume of fluid from the dental patient's mouth, the evacuator tube piece being sized for connection with the enlarged one end of the evacuator device.

16. The dental apparatus of claim 11 wherein the evacuator device has a small diameter one end for handling a small volume of fluid from the dental patient's mouth, wherein the evacuator tube piece being sized for connection with the small diameter one end of the evacuator device.

* * * * *